US009759832B1

(12) United States Patent
Freedman et al.

(10) Patent No.: US 9,759,832 B1
(45) Date of Patent: Sep. 12, 2017

(54) APPARATUS AND METHODS FOR FAST NMR WELL LOGGING WITHOUT INSTRUMENT SPEED EFFECTS

(71) Applicant: Schlumberger Technology Corporation, Sugar Land, TX (US)

(72) Inventors: Robert Freedman, Houston, TX (US); Henry Bachman, Sugar Land, TX (US); Anatoly Dementyev, Sugar Land, TX (US); Reza Taherian, Missouri City, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/131,185

(22) Filed: Apr. 18, 2016

(51) Int. Cl.
| | |
|---|---|
| *G01V 3/32* | (2006.01) |
| *G01V 3/34* | (2006.01) |
| *G01N 24/12* | (2006.01) |
| *G01N 24/08* | (2006.01) |
| *G01R 33/28* | (2006.01) |
| *G01R 33/46* | (2006.01) |
| *G01R 33/565* | (2006.01) |
| *G01R 33/38* | (2006.01) |

(52) U.S. Cl.
CPC ........... *G01V 3/32* (2013.01); *G01N 24/08* (2013.01); *G01N 24/12* (2013.01); *G01V 3/34* (2013.01); *G01R 33/282* (2013.01); *G01R 33/3808* (2013.01); *G01R 33/46* (2013.01); *G01R 33/56563* (2013.01)

(58) Field of Classification Search
None
See application file for complete search history.

(56) References Cited

U.S. PATENT DOCUMENTS

| | | | | |
|---|---|---|---|---|
| 4,710,713 | A | | 12/1987 | Strikman |
| 6,121,773 | A | * | 9/2000 | Taicher ................ G01V 3/32 324/300 |
| 6,140,818 | A | | 10/2000 | Hurlimann |
| 6,268,726 | B1 | * | 7/2001 | Prammer ............... G01V 3/32 324/300 |
| 6,285,901 | B1 | * | 9/2001 | Taicher ................ A61B 5/055 324/309 |
| 6,637,524 | B2 | | 10/2003 | Kruspe et al. |
| 6,838,875 | B2 | | 1/2005 | Freedman |
| 2002/0153888 | A1 | * | 10/2002 | Kruspe .............. E21B 33/1243 324/303 |

(Continued)

OTHER PUBLICATIONS

Freeman, "Advances in NMR Logging", JPT, SPE 89177, Jan. 2006 pp. 60-66.

*Primary Examiner* — Leon-Viet Nguyen
(74) *Attorney, Agent, or Firm* — Michael Dae (57) ABSTRACT

An apparatus for NMR properties of subsurface formations includes a magnet, a transmitter antenna and at least one of a receiver section of the transmit antenna or a separate receiver antenna having a length along the longitudinal dimension of the apparatus which is shorter than a length of the transmitter antenna along the longitudinal dimension. The apparatus includes circuitry for applying radio frequency current pulses to the entire transmitter antenna and for receiving signals by the at least one of the receiver section of the transmitter antenna and the separate receiver antenna.

19 Claims, 7 Drawing Sheets

(56) References Cited

U.S. PATENT DOCUMENTS

| | | | | |
|---|---|---|---|---|
| 2007/0257679 A1* | 11/2007 | Fanini | ...................... | G01V 3/28 324/366 |
| 2008/0174313 A1* | 7/2008 | Ganesan | .............. | G01N 24/081 324/313 |
| 2009/0018775 A1* | 1/2009 | Tabarovsky | ............. | G01V 3/28 702/9 |

* cited by examiner

APPARATUS AND METHODS FOR FAST NMR WELL LOGGING WITHOUT INSTRUMENT SPEED EFFECTS

CROSS REFERENCE TO RELATED APPLICATIONS

Not Applicable

STATEMENT REGARDING FEDERALLY SPONSORED RESEARCH OR DEVELOPMENT

Not Applicable

NAMES OF THE PARTIES TO A JOINT RESEARCH AGREEMENT

Not Applicable.

BACKGROUND

This disclosure relates to the field of nuclear magnetic resonance (NMR) well logging apparatus and methods. More specifically, the disclosure relates to methods and apparatus for NMR well logging that can make accurate measurements of NMR properties of formations surrounding a well at greater speed of motion of the well logging instrument without degradation of the measurements as a result of motion of the well logging instrument.

NMR-based measurement of the fractional volume of pore space (porosity) of subsurface formations, which is substantially independent of the rock mineral composition (matrix) of the subsurface formations, has been widely accepted. In complex environments, where the matrix properties are not well known, NMR measurements may provide more accurate porosities than other well logging instruments used to determine porosity. In addition, NMR transverse relaxation time ($T_2$) distributions may provide additional information about bound-fluid porosities and reservoir quality. Notwithstanding the superior quality of NMR porosity measurements, NMR well logging remains a niche service. One reason that has hindered NMR well logging from becoming a more widely used service for determination of subsurface formation properties is the relatively slow logging speeds that may be used with NMR instruments known in the art compared to that of other porosity tools.

NMR-determined porosities and $T_2$ distributions are adversely affected by speed of motion of the well logging instrument along a wellbore. Speed effects are more problematic with NMR measurements because of the fact that NMR measurements take a relatively long time (e.g., seconds) compared to other logging tool measurements. Logging speeds for NMR well logging instruments known in the art are relatively slow, e.g., typically in the range from 300 to 900 feet per hour depending on the logging environment and the specific application.

There exists a need for NMR well logging instruments and measurement techniques that can measure accurate porosities and $T_2$ distributions at much greater speeds, for example, 1800 feet per hour as may be used with gamma-gamma density porosity and neutron porosity well logging instruments.

SUMMARY

An apparatus for NMR properties of subsurface formations according to one aspect of the present disclosure includes a magnet, a transmitter antenna and at least one of a receiver section of the transmit antenna or a separate receiver antenna having a length along the longitudinal dimension of the apparatus which is shorter than a length of the transmitter antenna along the longitudinal dimension. The apparatus includes circuitry for applying radio frequency current pulses to the entire transmitter antenna and for receiving signals by the at least one of the receiver section of the transmitter antenna and the separate receiver antenna.

A method for measuring nuclear magnetic resonance (NMR) properties of subsurface formations according to another aspect of the present disclosure includes inducing a static magnetic field in the formation for pre-polarizing nuclear spins. A plurality of radio frequency current pulses is passed through a transmitter antenna. NMR signals are detected by at least one of a receiver portion of the transmitter antenna and a separate receiver antenna. The at least one of a receiver section and the separate receiver antenna has a length which is shorter than a length of the transmitter antenna along a longitudinal dimension of the transmitter antenna.

Other aspects and advantages will be apparent from the description and claims that follow.

DETAILED DESCRIPTION

Figure 1A:
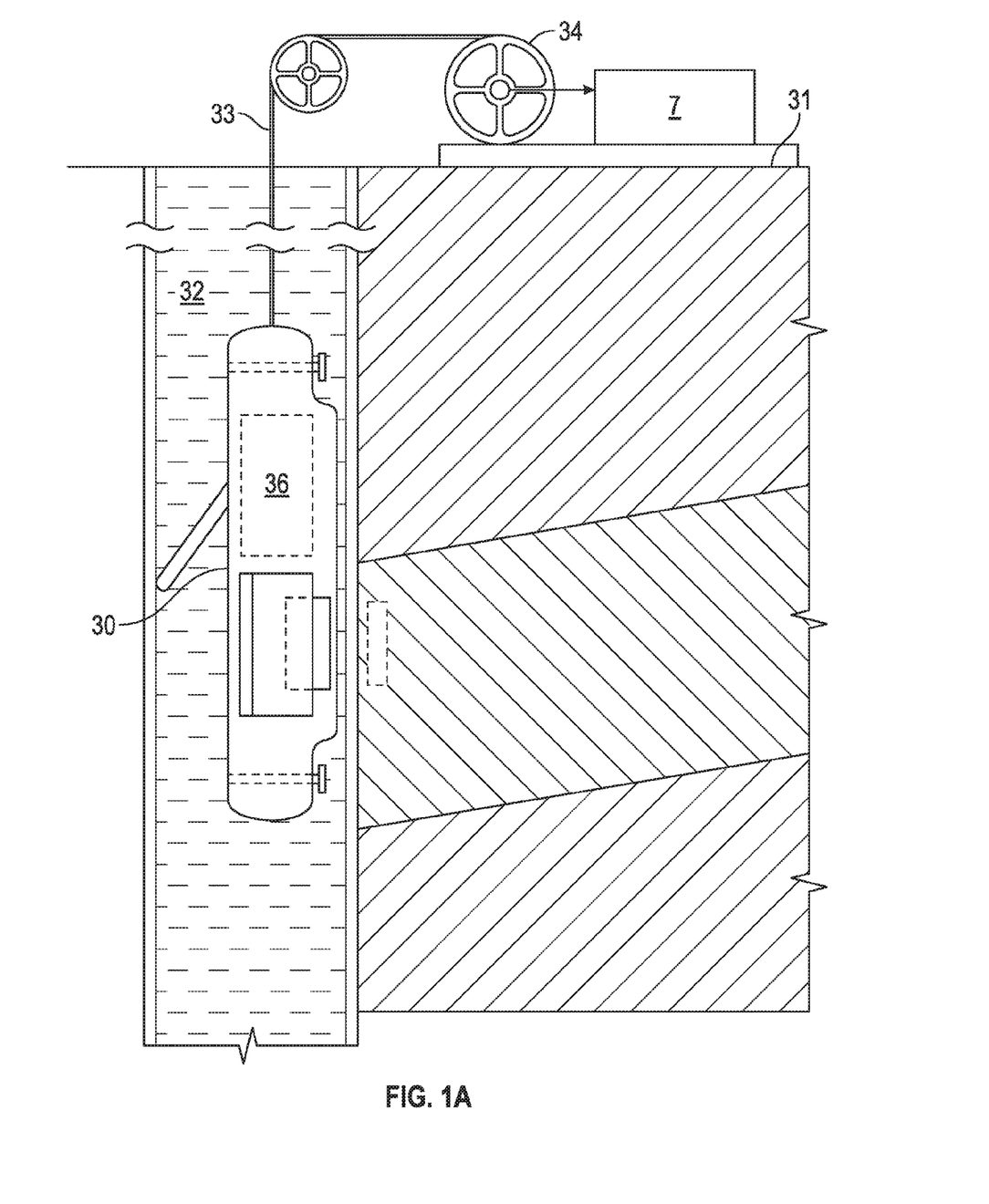
FIG. 1A shows an example wireline, slickline or coiled tubing conveyed NMR well logging instrument moving along the interior of a wellbore drilled through subsurface formations.

FIG. 1A shows an example embodiment of an apparatus for investigating subsurface formations 31 penetrated by a wellbore 32, which can be used in performing various embodiments of a method according to the present disclosure. A well logging instrument 30 may be suspended in the borehole 32 on an armored electrical cable 33, the length of which substantially determines the relative depth of the well logging instrument 30. The cable 33 may be extended into the wellbore 32 and withdrawn therefrom by suitable means at the surface such as a drum and winch mechanism 34. It will be appreciated that other conveyance devices for moving the well logging instrument 30 such as slickline or coiled tubing may also use a winch mechanism as shown in FIG. 1A. Surface equipment, represented at 7, can be of any type know in the art for operation well logging instruments, and may include a processor subsystem, signal communication and recording devices and a telemetry transceiver for communicating with the well logging instrument 30.

The well logging instrument which makes the measurements can be any suitable NMR well logging device, for use in "wireline" conveyed well logging instrumentation as shown in FIG. 1A, or of a type that can be used in logging while drilling (LWD) applications to be explained below with reference to FIG. 1B. The well logging instrument 30 includes, for example, a magnet such as a permanent magnet, magnet array, electromagnet or combinations thereof for inducing a static magnetic field in the formations 31, and one or more radio frequency (RF) antennas for inducing a pulsed RF magnetic field in the formations 31 and for receiving RF energy induced by NMR phenomena excited in the formations 31.

The well logging instrument described above can also be implemented, for example, in logging-while-drilling ("LWD") equipment. As shown, for example, in FIG. 1B, a platform and derrick 210 are positioned over a wellbore 212 that may be formed in the Earth by rotary drilling. A drill string 214 may be suspended within the borehole and may include a drill bit 216 attached thereto and rotated by a rotary table 218 (energized by means not shown) which engages a kelly 220 at the upper end of the drill string 214. The drill string 214 is typically suspended from a hook 222 attached to a traveling block (not shown). The kelly 220 may be connected to the hook 222 through a rotary swivel 224 which permits rotation of the drill string 214 relative to the hook 222. In some embodiments, the drill string 214 and drill bit 216 may be rotated from the surface by a "top drive" type of drilling rig.

Drilling fluid or mud 226 is contained in a mud pit 228 adjacent to the derrick 210. A pump 230 pumps the drilling fluid 226 into the drill string 214 via a port in the swivel 224 to flow downward (as indicated by the flow arrow 232) through the center of the drill string 214. The drilling fluid exits the drill string via ports in the drill bit 216 and then circulates upward in the annular space between the outside of the drill string 214 and the wall of the wellbore 212, as indicated by the flow arrows 234. The drilling fluid 226 thereby lubricates the bit and carries formation cuttings to the surface of the earth. At the surface, the drilling fluid is returned to the mud pit 228 for recirculation. If desired, a directional drilling assembly (not shown) could also be employed.

A bottom hole assembly ("BHA") 236 may be mounted within the drill string 214, in some cases near the drill bit 216. The BHA 236 may include subassemblies for making measurements, processing and storing information and for communicating with the Earth's surface. Such measurements may correspond to those made using the NMR well logging instrument explained above with reference to FIG. 1A. The bottom hole assembly is typically located within several drill collar lengths of the drill bit 216. In the illustrated BHA 236, a stabilizer collar section 238 is shown disposed immediately above the drill bit 216, followed in the upward direction by a drill collar section 240, another stabilizer collar section 242 and another drill collar section 244. This arrangement of drill collar sections and stabilizer collar sections is illustrative only, and other arrangements of components in any implementation of the BHA 236 may be used. The need for or desirability of the stabilizer collars will depend on drilling conditions as well as on the demands of the measurement.

Figure 1B:
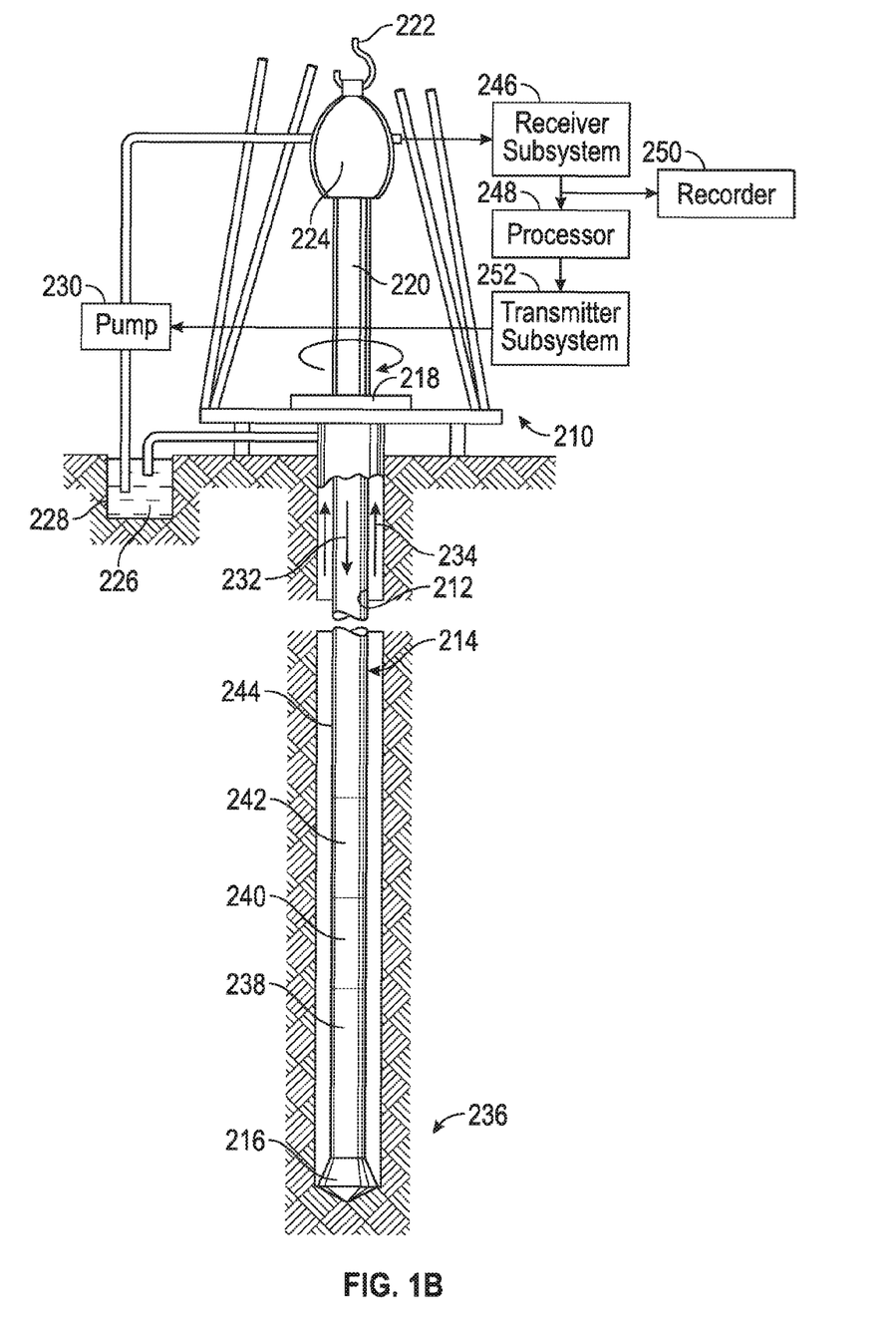
FIG. 1B shows an example logging while drilling (LWD) NMR logging instrument.

In the arrangement shown in FIG. 1B, the components of the NMR well logging instrument may be located, for example, in the drill collar section 240 above the stabilizer collar 238. Such components could, if desired, be located closer to or farther from the drill bit 216, such as, for example, in either stabilizer collar section 238 or 242 or the drill collar section 244.

The BHA 236 may also include a telemetry subassembly (not shown) for data and control communication with the Earth's surface. Such telemetry subassembly may be of any suitable type, e.g., a mud pulse (pressure or acoustic) telemetry system, wired drill pipe, etc., which receives output signals from LWD measuring instruments in the BHA 236 (including the NMR well logging instrument) and transmits encoded signals representative of such outputs to the surface where the signals are detected, decoded in a receiver subsystem 246, and applied to a processor 248 and/or a recorder 250. The processor 248 may comprise, for example, a suitably programmed general or special purpose processor. A surface transmitter subsystem 252 may also be provided for establishing downward communication with the bottom hole assembly.

The BHA 236 may also include conventional acquisition and processing electronics (not shown) comprising a microprocessor system (with associated memory, clock and timing circuitry, and interface circuitry) capable of timing the operation of the source and the data measuring sensors, storing data from the measuring sensors, processing the data and storing the results, and coupling any desired portion of the data to the telemetry components for transmission to the surface. The data may also be stored in the instrument and retrieved at the surface upon removal of the drill string. Power for the LWD instrumentation may be provided by battery or, as known in the art, by a turbine generator disposed in the BHA 236 and powered by the flow of drilling fluid. The LWD instrumentation may also include directional sensors (not shown separately) that make measurements of the geomagnetic orientation or geodetic orientation of the BHA 236 and the gravitational orientation of the BHA 236, both rotationally and axially.

The foregoing computations may be performed on a computer system such as one shown in the processor at 248 in FIG. 1B, or in the surface unit 7 in FIG. 1A. However, any computer or computers may be used to equal effect.

Figures 2A, 2B:
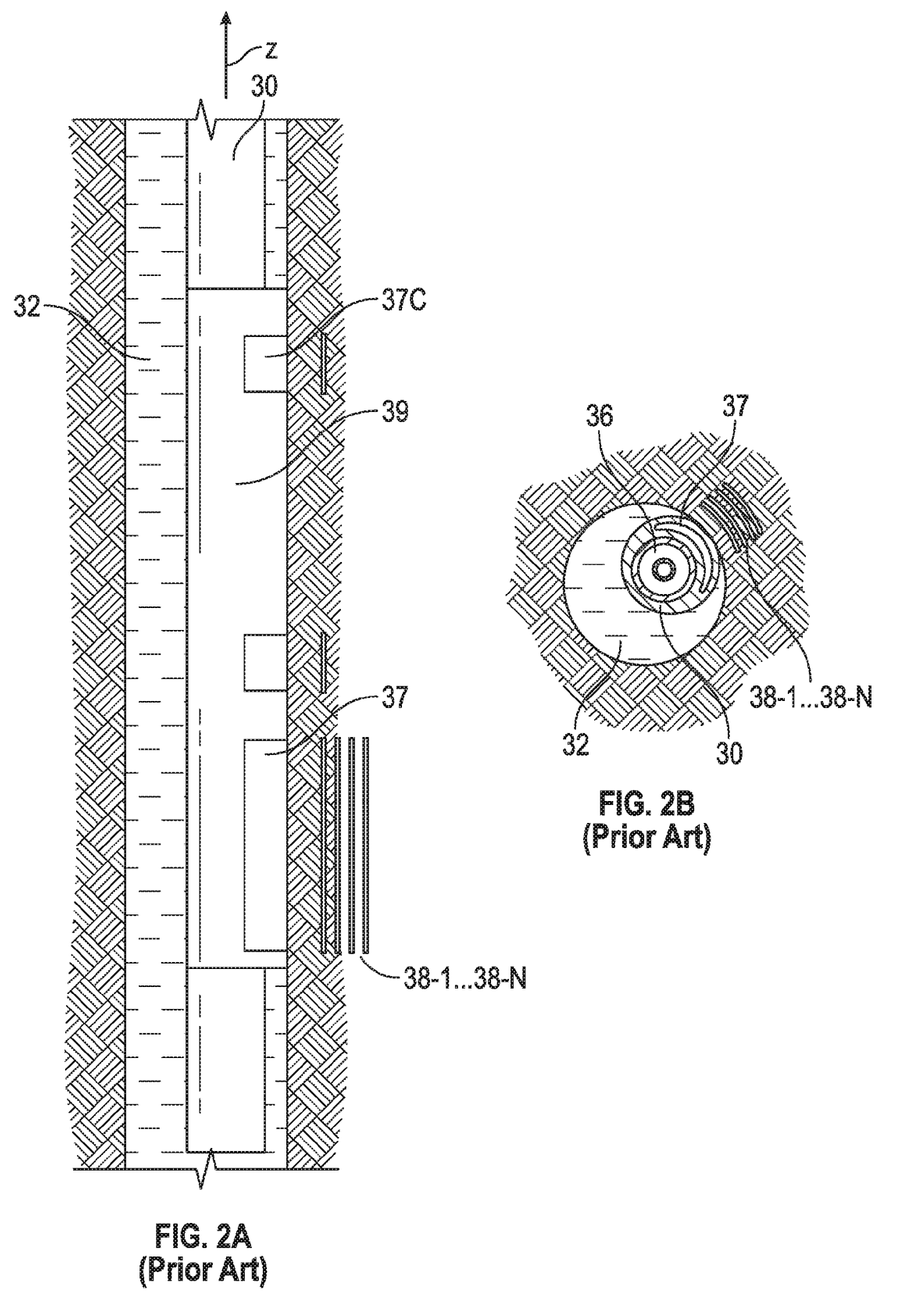
FIG. 2A shows a schematic representation of some components of an example embodiment of an NMR well logging instrument.
FIG. 2B shows a horizontal cross-section of the well logging instrument of FIG. 2A wherein different zones in the formation are shown that may be separately and individually excited to make NMR measurements therein.
Figure 2C:
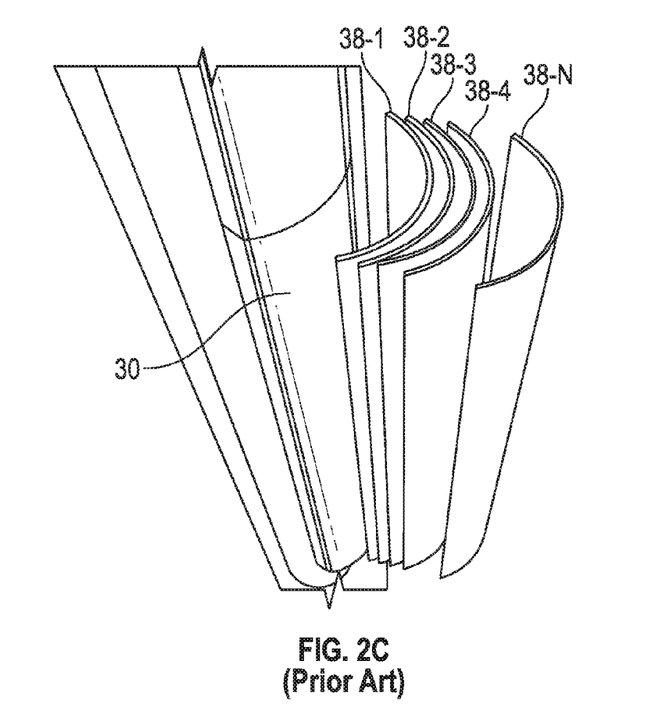
FIG. 2C shows an oblique view of the instrument of FIG. 2A to more clearly illustrate the different zones of FIGS. 2A and 2B.

The present example embodiment of NMR well logging instrument may be of a type that can be operated to obtain separate measurements from a plurality of closely spaced thin, cylindrical or other shape "shell"-like regions in the surrounding formations 31. A simplified representation of some of the components of a suitable type of well logging instrument is shown in FIGS. 2A, 2B and 2C. FIG. 2A shows a side view of the NMR well logging instrument 30. The example NMR well logging instrument shown in FIG. 2A may be one such as sold under the trademark MR SCANNER, which is a trademark of Schlumberger Technology Corporation, Sugar Land, Tex. A magnet or magnet array (magnet) is shown at 36. The magnet 36 may be a permanent magnet, magnet array, an electromagnet or any combination of the foregoing. An RF antenna, represented at 37, may be a suitably oriented wire coil or coils. The MR SCANNER instrument may include a separate RF antenna 37C, however this separate antenna is not important for purposes of explaining apparatus and methods according to the present disclosure.

FIG. 2A also illustrates a general representation of the type of closely spaced cylindrical thin shells, 38-1, 38-2, . . . 38-N, that can be selectively excited to produce NMR phenomena using a multi-frequency transmitter and receiver circuit. As is known in the art, for example as disclosed in U.S. Pat. No. 4,710,713 issued to Strickman, the well logging instrument may be programmed select the shell region to be investigated by appropriately selecting the frequency of the RF energy in the current pulses applied to the antenna 37. The magnet 36 may be arranged such that a static magnetic field induced in the formations (31 in FIG. 1) has substantially equal amplitude along the longitudinal dimension of the magnet 36, and in some embodiments, the amplitude of the static magnetic field may change with respect to lateral distance from the magnet 36. The RF antenna 37 may be arranged such that RF magnetic fields induced in the formations by passing pulses of RF current through the antenna 37 are substantially orthogonally polarized with reference to the polarization direction of the static magnetic field. The RF magnetic fields induced by the antenna 37 may also have substantially equal amplitude along the longitudinal dimension of the antenna 37 and the magnet 36. Similarly, the sensitivity distribution of the antenna 37 may be such that the antenna 37 has substantially equal sensitivity along the longitudinal dimension of the antenna 37. Longitudinal dimension as used in the present context is used to mean along a line parallel to the longitudinal axis of the well logging instrument 30, shown approximately by the arrow labeled Z in FIG. 2A.

The well logging instrument 30 may comprise circuitry for applying pulses of RF current through the antenna 37 and for detecting voltages induced in the antenna 37, of the well logging instrument 30. A non-limiting example embodiment of suitable circuitry is described in the Strickman '713 patent referred to above. The exact configuration of the circuitry is not intended to limit the scope of the present disclosure; those skilled in the art will be able to design different forms of suitable circuitry for use in the well logging instrument 30.

In a well logging instrument and method according to the present disclosure, the relative longitudinal dimensions of the antenna or antennas may be selected differently during the transmit phase compared to the receive phase, as will be further explained. An apparatus and method according to the present disclosure results in exciting NMR phenomena in the selected regions of the formations 31 and detecting signals resulting from such NMR phenomena only in longitudinal portions that are substantially unaffected by movement of the well logging instrument 30 along the wellbore 32. The different selected regions of the formations 31 are shown schematically in FIGS. 2A and 2B at 38-1 . . . 38-N. FIG. 2C shows an oblique view of the well logging instrument 30 to more clearly show the lateral separation within the formations 31 of the selected regions 38-1, 38-2, 38-3, 38-4, . . . 38-N.

1. Description of Speed Effects

There are two independent types of speed effects observed on NMR porosity and $T_2$ distribution logs acquired at relatively fast logging speeds.

The first effect is caused by incomplete pre-polarization of the hydrogen nuclei by the static magnetic field induced by the magnet in the well logging instrument (e.g., as shown at 36 in FIG. 2A). Incomplete pre-polarization may result in underestimation of the total porosity; such effect is increased in formations which have substantial porosity with long longitudinal ($T_1$) relaxation times of fluid filling the pore spaces. To measure accurate total porosities it is desirable that the susceptible nuclei being excited to induce NMR phenomena, e.g., hydrogen nuclei, be exposed to the static magnetic field for a sufficient time to obtain 95% (i.e., exposure times of at least 3 $T_1$) or greater pre-polarization prior to the start of the NMR measurement. To obtain this level of pre-polarization while moving the well logging instrument at relatively high speeds, non-overlapping measurements are conducted. For non-overlapping measurements the hydrogen nuclei may be pre-polarized by a magnet that has sufficient length along the direction of motion to obtain full polarization. The pre-polarization magnet length depends on the desired maximum logging speed and the maximum $T_1$ of the fluids in the formations to be polarized. The extent of pre-polarization that is actually obtained in any set of circumstances is related to the instrument speed and the maximum $T_1$. The magnitude of the pre-polarization will be further explained below for different instrument designs, e.g., pre-polarization and antenna lengths. The term pre-polarization is used in present context to mean orientation of the nuclear spin axes of susceptible nuclei along the polarization direction of the static magnetic field induced by the magnet (36 in FIG. 2).

The second effect of logging speed is to compress the measured or apparent $T_2$ distributions. Such compression of measured $T_2$ distributions is greater for longer $T_2$ times. Compression does not affect the apparent total NMR porosity; however, it leads to errors in calculated bound-fluid and free-fluid porosities. The compression effect results from longitudinal movement of the RF antenna during the NMR measurement away from the region of the formation where transverse magnetization was induced by imparting RF magnetic fields into the formation. The compression effect can be mitigated to some extent by using a larger RF antenna (larger being with reference to the direction of motion of the instrument during measurement); however, it remains a substantially adverse effect for practical antenna lengths and speeds of 1800 feet per hour. 1800 feet per hour is a practical instrument speed for other types of porosity measurements, e.g., gamma-gamma density porosity and neutron porosity.

Figure 3:
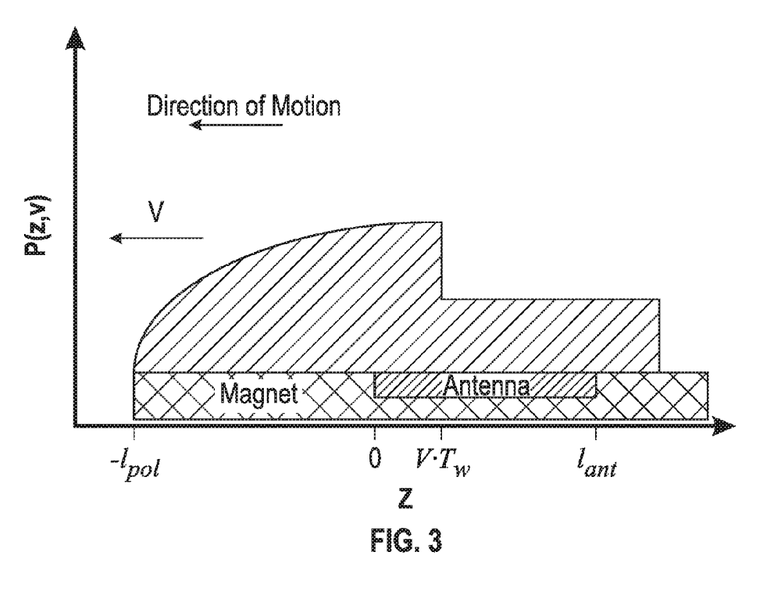
FIG. 3 shows a model of the polarization profile for an example embodiment of a well logging instrument moving at constant speed along a wellbore.

2. Speed Effects on NMR Polarization 2.1 Polarization Effects for an Instrument Moving in a Constant Amplitude (with Respect to Direction of Motion) Static Magnetic Field Below will be explained the average speed-dependent polarization over the length of the RF antenna. A schematic representation of a model NMR well logging instrument is shown in FIG. 3. The modeled instrument is moving at constant speed (v). On the y-axis is the speed and position dependent polarization profile shown over the length of the modeled instrument. In FIG. 3 it is assumed that the static magnetic field produced by the magnet is substantially constant amplitude with reference to the direction of motion (i.e., the longitudinal dimension) of the magnet. The polarization profile shown is for an instrument that has moved a distance $v \cdot T_w$ since the end of the previous measurement. The time $T_w$ is the wait time between the end of one NMR measurement and the start of the next NMR measurement. A portion of the length $v \cdot T_w$ of the antenna in the direction of motion has been pre-polarized by the pre-polarization length $l_{pol}$ of the magnet whereas the remaining length of the antenna, $l_{ant} - v \cdot T_w$, has been re-polarized by the static magnetic field during the time $T_w$ from the end of the previous NMR measurement. FIG. 3 shows a snapshot of the spin polarization in the formation at the instant before a new NMR measurement is initiated by application of a 90° RF pulse (explained further below) to the antenna.

The speed and position dependent polarization profile is given by the equations, $$P(z, v) = 1 - \exp\left(-\frac{T(z, v)}{T_1}\right) \quad (1)$$

where $$T(z, v) = T_w, \text{ for } vT_w \le z \le l_{ant}, \quad (2a)$$

and $$T(z, v) = \frac{l_{pol} + z}{v}, \text{ for } 0 \le z \le vT_w. \quad (2b)$$

FIG. 3 and the above equations are valid for the general case of overlapping NMR measurements. In the region of the antenna in Eq. (2a) the instant NMR measurements overlap (i.e., two NMR measurements measure part of the same longitudinal interval) with the previous measurements whereas in the region in Eq. (2b) successive NMR measurements are non-overlapping. From Eq. (1) and the fact that $T_1$ values in many formations are several seconds, wait times of $3T_1$ may be used to attain 95% polarization. Such long wait times would lead to very slow logging speeds. Therefore, using known apparatus and methods, measurements over the total length of the RF antenna are used for fast NMR logging without overlap. The condition for non-overlapping measurements is that $v \cdot T_w = l_{ant}$. In the following description the notation may be simplified by replacing $l_{ant}$ with $l_a$.

The average speed-dependent polarization over the length of the antenna may be determined by a weighted average of the speed and position dependent polarization function over the antenna such as by the following expression:

$$P(v) = \int_0^{l_a} S_a(z) P(z, v) dz = \int_0^{l_a} P(z, v) \frac{dz}{l_a}, \quad (3)$$

where in the integral on the right hand side of Eq. (3), to simplify the description, it is assumed that the antenna sensitivity function, $S_a(z) = l_{ant}^{-1}$, is uniform along the longitudinal dimension of the antenna. Using Eqs. (1) and (2) the polarization may be determined by the expression:

$$P(v) = \quad (4)$$
$$\frac{vT_w}{l_a} - \frac{vT_1}{l_a}\left(1 - \exp\left(-\frac{T_w}{T_1}\right)\right)\exp\left(-\frac{l_p}{vT_1}\right) + \left(1 - \exp\left(-\frac{T_w}{T_1}\right)\right)\frac{(l_a - vT_w)}{l_a}$$

The last term in Eq. (4) accounts for the overlapping part of the measurement where the hydrogen nuclei from the previous NMR measurement are repolarized by the static magnetic field during the wait time. It is desired to obtain non-overlapping measurements for relatively high instrument movement speeds for $v \cdot T_w = l_{ant}$ which may be represented by the expression:

$$P(v) = 1 - \frac{1}{r}(1 - \exp(-r))\exp\left(-\frac{l_p}{l_a}r\right), \quad (5)$$

where the ratio r may be defined as:

$$r = \frac{T_w}{T_1} \equiv \frac{l_a}{vT_1}. \quad (6)$$

It may be observed in Eq. (5) that the average polarization over the length of the antenna depends on the two dimensionless ratios, r and $l_p/l_a$. Moreover, for a given well logging instrument configuration with fixed values for $l_p$ and $l_a$ the average polarization depends only on the product, $v \cdot T_1$, i.e., the distance the instrument moves during the time $T_1$. In subsurface formations there is a distribution of $T_1$ times corresponding to different pores sizes and fluids. If a selected value of polarization, e.g., 95%, is obtained for a certain value of $T_1$ then formations having shorter values of $T_1$ will have polarization that exceeds 95%.

Figure 4:
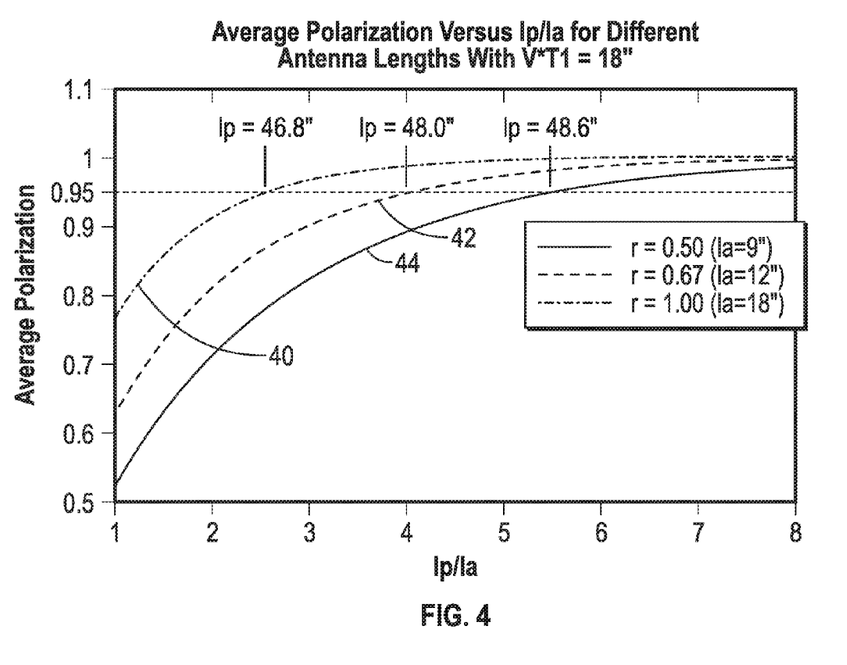
FIG. 4 shows plots of average polarization versus $l_p/l_a$ for different values of the parameter $r=l_a/v*T_1$ for $v \cdot T_1=18$ inches.

FIG. 4 shows plots of the average polarization given by Eq. (5) with respect to the ratio $l_p/l_a$ for values of the ratio r=1 at curve 40, r=0.67 at curve 42 and r=0.50 at curve 42 for a value of $v \cdot T_1 = 18$ inches. It is convenient for purposes of the present description to express v in inches per second and $T_1$ in seconds. For a tool moving at 1800 feet per hour (6 inches per second) the plots in FIG. 4 are valid for a value of $T_1 = 3$ seconds.

The three curves in FIG. 4 correspond to antenna lengths of 9, 12, and 18 inches. It may be observed that for all three antenna lengths a pre-polarization length of approximately 48 inches provides 95% pre-polarization. Note that less pre-polarization length is used for longer antenna lengths.

Some additional results for non-overlapping measurements computed from Eq. (5) are shown in Table 1.

TABLE 1

Average Polarization for Non-Overlapping Measurements (v * Tw = la) v = 1800 feet per hour in a formation with $T_1$ = 3 seconds v * $T_1$ = 18 inches

| $l_p$ (in.) | $l_a$ (in.) | $l_p/l_a$ | r = la/v * $T_1$ | P(v) |
| --- | --- | --- | --- | --- |
| 54 | 18 | 3 | 1 | 0.97 |
| 54 | 12 | 4.5 | 0.67 | 0.96 |
| 48 | 18 | 2.67 | 1 | 0.96 |
| 48 | 12 | 4 | 0.67 | 0.95 |
| 36 | 18 | 2 | 1 | 0.91 |
| 36 | 12 | 3 | 0.67 | 0.90 |

It may be observed in Table 1 that to obtain 95% or greater pre-polarization at 1800 feet per hour well logging instrument speed where $T_1=3$ seconds would have a magnet pre-polarization length of 48 inches or greater.

Having explained the effect of instrument motion on polarization, methods and apparatus according to the present disclosure may now be better understood. It should be emphasized that Table 1 shows respective values for non-overlapping measurements (as defined above). Given the amount of time for acquiring NMR measurements, and given that NMR RF pulsing reduces some or all of the static field-induced magnetization in front (front being with respect to direction of motion) of the antenna (e.g., 37 in FIG. 2A), the only way for known NMR apparatus to make non-overlapping measurements is to stop applying RF current pulses to the antenna and wait for the instrument to move one sensor length (i.e., the length of the antenna). In practice, skipping such a large axial portion of formation is not desirable, and thus a compromise is made to allow for an "overlapped" region of the formation in combination with the non-overlapped part of the measurement. The overlapped region may take a substantial amount of wait time to re-polarize the nuclear spins, which in turn slows down logging. This limitation is one of the bases for apparatus and methods according to the present disclosure.

3. Instrument Speed Effects on $T_2$

The effect of well logging instrument speed on NMR spin-echo amplitude decay is to increase the apparent spin echo amplitude decay rate. This means that the apparent or observed $T_2$ values are reduced compared to the true values that would be measured by a stationary tool. The $T_2$ speed effect can be better understood by considering FIG. 5, which shows two positions of the RF antenna at times separated by dt as the tool moves in the direction shown at a constant speed, v.

Figure 5:
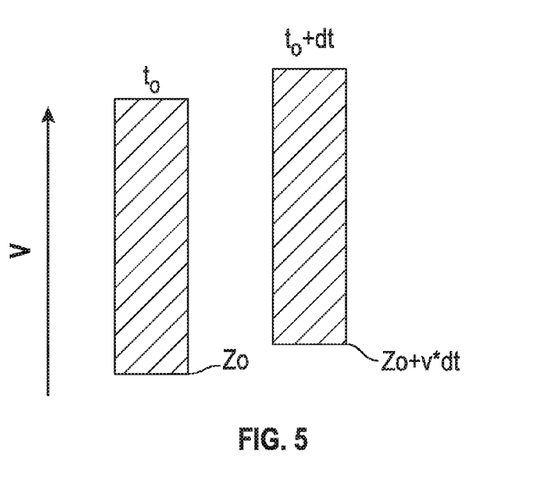
FIG. 5 shows two positions of a prior art NMR tool RF antenna for an instrument moving with speed v.

At time $t_o$ in FIG. 5, a radio frequency current pulse is passed through the first RF antenna (see, e.g., 37 in FIG. 2A) having duration and amplitude selected to reorient the nuclei by 90° (the NMR excitation pulse) and thus creates a transverse magnetization in the formation adjacent to the antenna, wherein transverse is with reference to the direction of the static magnetic field induced by the magnet (36 in FIG. 2A). At time $t_o+dt$ the antenna has moved a distance v*dt away from the volume where the transverse magnetization was induced by the RF magnetic field at time $t_o$. To measure spin echo amplitude decay, the 90° RF current pulse may be followed by a plurality of RF current pulses passed through the antenna, wherein each such pulse has a duration and amplitude selected to reorient the nuclear magnetic spin axes of the susceptible nuclei by 180° each such current pulse separated by a spin echo time TE. RF signals generated by NMR spin echoes following the 180° RF pulses are detected and their amplitudes represent the spin echo amplitude decay rate. Motion of the instrument during the time span of the 180° RF pulses that follow the 90° excitation pulse is the cause of the $T_2$ speed effect.

During the acquisition of the spin-echoes, which can take one second or more, the instrument moves into a region that has no transverse magnetization and therefore as subsequent spin echoes are acquired the spin echo signal is reduced by the loss of transverse magnetization. FIG. 5 shows the instrument positions at times $t_o$ and $t_o+dt$. If the transverse magnetization created at time $t_o$ corresponds to the length of the instrument shown in FIG. 5, it is apparent that when the instrument is moved to a new position at time $t_o+dt$ as shown, the antenna will be at least in part positioned adjacent an area of the formation for which no transverse magnetization has occurred. Such position-related loss of transverse magnetization, and therefore signal amplitude for this simple model shown in FIG. 5 may be expressed as:

$$dM = -\frac{vdt}{l_a}M \tag{11}$$

and by integration the transverse magnetization at time t may be determined by the expression:

$$M(t) = M(t_o)\exp\left(-\frac{v(t-t_o)}{l_a}\right) \tag{12}$$

Eq. (12) indicates that the speed-affected $T_2$ related spin echo amplitude decay time is given by $T_{2v}=l_a/v$ and that during well logging the apparent or measured decay rate may be expressed as:

$$\frac{1}{T_{2a}} = \frac{1}{T_2} + \frac{1}{T_{2v}} \equiv \frac{1}{T_2} + \frac{v}{l_a} \tag{13}$$

The $T_2$ related spin echo amplitude decay speed effect can be mitigated somewhat by using a longer RF antenna, however, it is still a substantial effect and represents an obstacle to accurate fast NMR well logging. Using Eq. (13) the apparent $T_2$ relaxation time (and/or values of such times used to calculate a $T_2$ distribution) may be represented as:

$$T_{2a} = \frac{T_2 \cdot T_{2v}}{T_2 + T_{2v}}, \tag{14}$$

Eq. (14) shows that the apparent relaxation time is less than the lesser of $T_2$ and $T_{2v}$. Table 2 shows the speed effect at 1800 feet per hour instrument speed (6 inches per second) for different antenna lengths. It may be observed in Table 2 that for longer values of $T_2$ the apparent values, $T_{2a}$, are substantially smaller than their actual values.

TABLE 2

$T_2$ Speed Effect at 1800 feet per hour

| $l_a$(in.) | $T_2$(s) | $T_{2a}$(S) |
|---|---|---|
| 6 | 1 | 0.5 |
| 6 | 3 | 0.75 |
| 12 | 1 | 0.67 |
| 12 | 3 | 1.2 |
| 15 | 0.5 | 0.42 |
| 15 | 1 | 0.71 |
| 15 | 2 | 1.1 |
| 15 | 3 | 1.4 |
| 18 | 0.5 | 0.43 |
| 18 | 1.0 | 0.75 |
| 18 | 2.0 | 1.2 |
| 18 | 3.0 | 1.5 |

4. Novel RF Antenna Design and Associated Pulse Sequences for Fast NMR Logging without $T_2$ Speed Effects A pre-polarization magnet with a flat (defined above) magnetic field profile and a length chosen to be in the range from 48 to 54 inches, depending on the RF antenna length and other requirements, was shown above to be suitable for fast NMR logging (e.g., at speeds up to 1800 feet per hour). The $T_2$ speed effect, however, would use a different antenna design to enable fast logging. In NMR well logging instrument designs known in the art prior to the present disclosure the same RF antenna length which is used to transmit RF pulses is also used to receive the NMR signals from the sensitive volume (the measurement region in FIG. 2) of the formation. There may be multiple RF antennas in conventional NMR tools (see, e.g., Freedman, R., "Advances in NMR Logging," p. 60-66, Journal Petroleum Technology, SPE 89177, 2006), however, the total length of the antenna in known multiple antenna instruments is used both to transmit RF pulses, and also to receive NMR signals from the formation (see 38-1, 38-2, 38-3 and 38-4 in FIG. 2B). During NMR well logging measurement when the well logging instrument is moving along a wellbore, the antenna moves away from the region where transverse magnetization was excited by the transmitted RF pulses and, as explained above, such movement causes the $T_2$ speed effect as explained with reference to FIG. 5.

Figure 6:
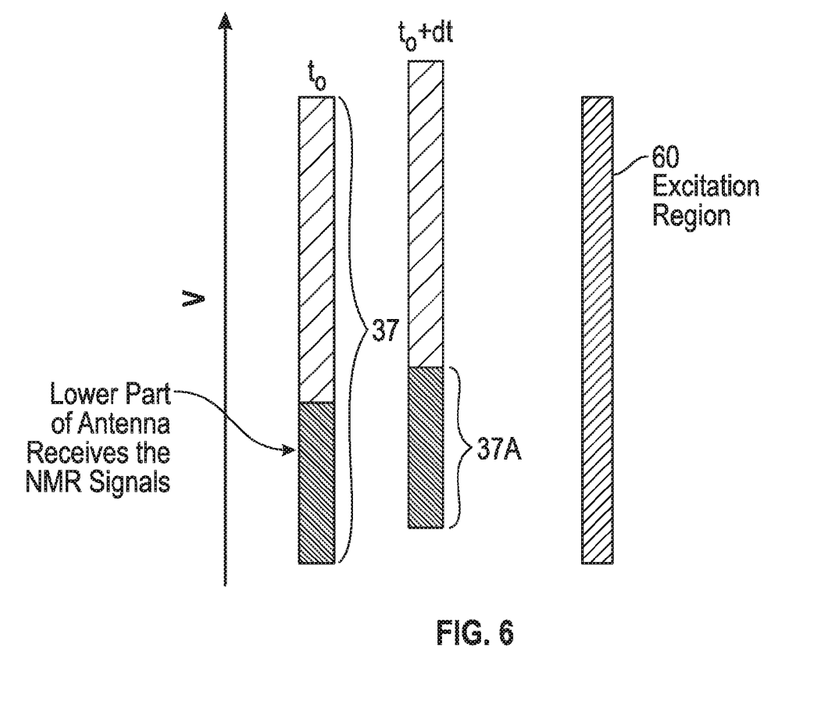
FIG. 6 shows two positions of an RF NMR antenna with the design disclosed herein for a tool moving with speed v. At time $t_o$ a 90° excitation pulse applied to the antenna creates a transverse magnetization in the formation adjacent to the antenna shown as the "excitation region" As the tool moves during time $t_o+dt$ the lower part of the antenna receives signal from formation which is consistently within the excitation region, so as the tool moves, there is no loss of transverse magnetization to cause the $T_2$ speed effect.
Figure 6A:
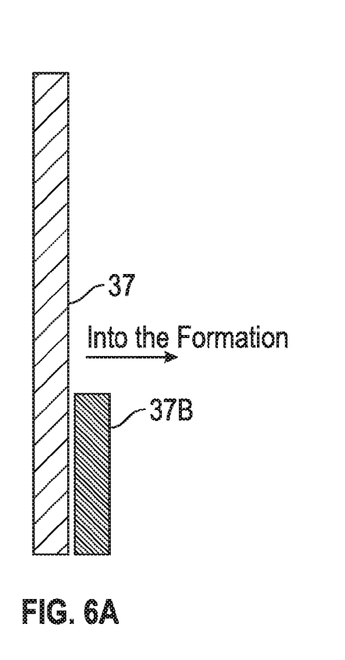
FIG. 6A shows a schematic view of an embodiment of an NMR well logging instrument having separate transmitter and receiver antennas.

As shown schematically in FIG. 6 and FIG. 6A, or single or multiple antennas may overcome spin echo signal amplitude reduction caused by the loss of transverse magnetization as a result of instrument motion. In FIG. 6 the schematic can be interpreted either as a single antenna with different portions, or two separate antennas which are juxtaposed end-to-end and simultaneously excited during transmit, while only the lower antenna is active during receive. FIG. 6A is an example of separate antennas juxtaposed side by side. In transmit mode the entire length 37 in FIG. 6, or the longer antenna as shown at 37B in FIG. 6A, may be used to transmit RF pulses, whereas in receive mode only the lower part of the antenna, i.e., the receiver section shown at 37A of FIG. 6, or the shorter antenna 37B of FIG. 6A is connected to receiver circuitry in the instrument, e.g., as shown at 39 in FIG. 2A, to detect NMR signals from the measurement region. Because the receiver section 37A of the antenna 37 in FIG. 6 (or a similar length separate antenna as shown at 37B in FIG. 6A) remains opposite and within the excited region 60 as the instrument moves there is no speed induced $T_2$ decay resulting from loss of transverse magnetization.

In the embodiment shown in FIG. 6 the receiver section 37A of the antenna 37 is active in receive mode while the remaining (upper) part of the antenna may be electrically shorted out, for example, during NMR signal acquisition. Several switching technologies can be used for shorting a portion of the antenna. While the switching times of reed relays and even solid state relays are, at best, on the order of 100's of microseconds, MOSFET switches feature turn-on times on the order of 100's nanoseconds. The ON resistance of the switch (Rds) can now be as low as 15 milliohms for a 650V rated MOSFET. This development opens up the possibility of using MOSFET switches inside the very sensitive NMR antenna circuit. It is to be clearly understood that the scope of the present disclosure is not limited to the embodiment shown in FIG. 6 and that in other embodiments two separate juxtaposed antennas may be used as shown at 37 and 37B in FIG. 6A, wherein the two antennas are in the same orientation or in different orientations. It should also be clearly understood that using the lower part of the antenna (e.g., receiver section 37A in FIG. 6) is appropriate for the case where the direction of motion of the NMR well logging instrument is toward the surface of the wellbore (up logging), i.e., toward shallower measured depth. In the case of moving the NMR well logging instrument away from the surface (down logging) the upper part of the antenna is appropriate. In the case of logging while drilling (LWD) instruments, wherein measurements may be made as the instrument moves in either the direction of shallower or greater measured depth, the receiver section of the antenna or a separate receiver antenna may be positioned substantially in the middle along the antenna or separate transmitter antenna.

Figure 6B:
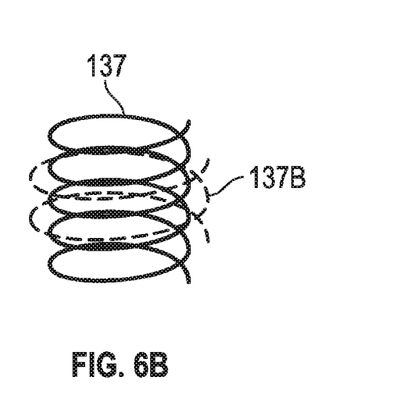
FIG. 6B shows a schematic view of an embodiment of NMR well logging instrument having separate transmitter and receiver antennas which are axially-concentric.

The NMR well logging instrument disclosed herein can be used with any conveyance methods, including without limitation armored electrical cable ("wireline"), on or in a well drilling assembly, (LWD), coiled tubing, downhole tractors, or slick line. For wireline NMR logging instruments, the $T_2$ speed effect (among other factors) limits the logging speed to be much slower than some other formation evaluation tools which can be logged at 1800 feet per hour or more. Using an instrument according to the present disclosure, NMR logging speeds can be increased and thus save rig time. For LWD NMR instruments, the logging speeds are considerably slower than for wireline conveyed instruments, but speed effects still exist. Specifically, the sensitive region is sometimes axi-symmetric and short. The extent of the parasitic $T_2$ speed effect depends on the rate of penetration of the drill bit and bottom hole assembly (BHA). Given the short sensitive region of LWD NMR well logging instruments, rates of penetration in excess of 100 feet per hour may show a $T_2$ speed effect which is unacceptably large. Similar arguments apply to logging while tripping or measurement after drilling. The antennas used in LWD NMR logging tools are typically of a circular coil design to achieve azimuthal symmetry. An example implementation of an NMR well logging instrument according to the present disclosure is that the transmitter coil and the receiver coils can be concentrically aligned as shown at 137 and 137B in FIG. 6B. Without departing from the scope of the present disclosure, the transmitter coil would be longer while the receiver coil would be shorter, spanning only a fraction of the length of transmitter coil.

Figure 7:
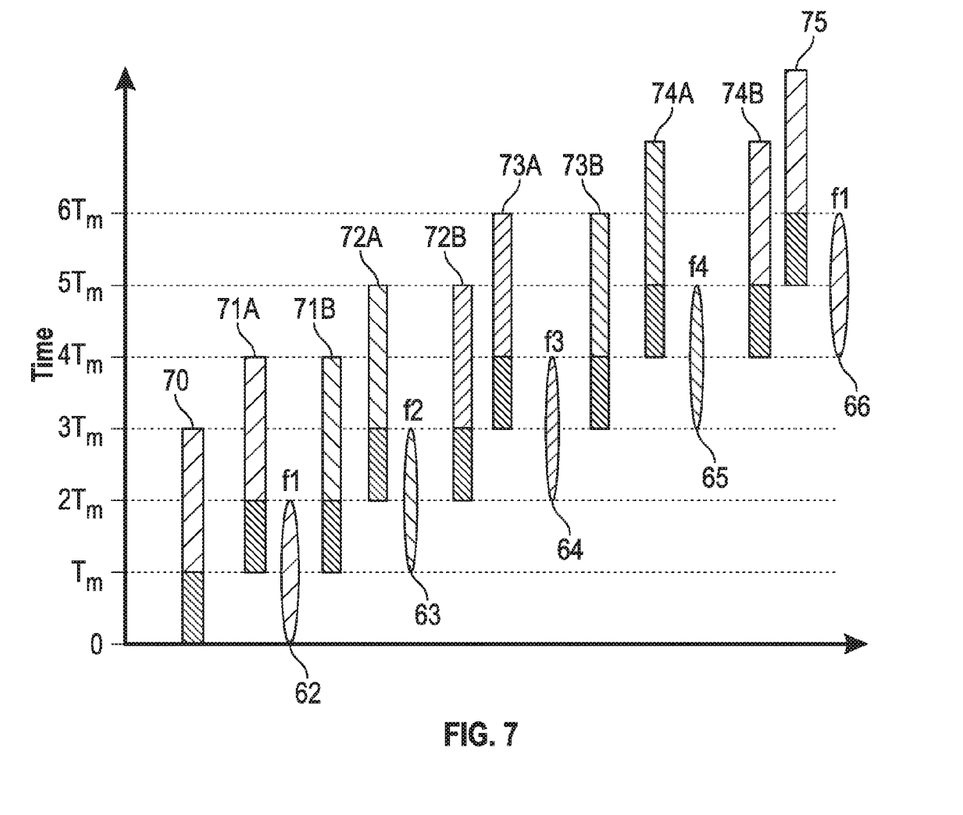
FIG. 7 shows an example of a multi-frequency NMR logging apparatus and associated pulse sequences for acquisition of NMR logging data without speed effects on the measured $T_2$ distributions caused by loss of transverse magnetization as the tool moves.

Consider a logging instrument moving with a constant speed v. FIG. 7 shows an example of how to use the antenna design as explained above with reference to FIG. 6, and an associated multi-frequency RF pulse sequence for fast NMR logging. In this example embodiment the receiver section (37A in FIG. 6) of the RF antenna is one third of the total length of the RF antenna (37 in FIG. 6). The measurement time $T_m$ is equal to the time used to acquire some or all of the NMR measurements, e.g., spin-echo amplitude measurements in a pulse sequence (or sequences) for estimating NMR properties of the formations. The pulse sequence entails applying a plurality of radio frequency current pulses and receiving the signals generated therein. During each $T_m$ the well logging instrument moves a distance $v*T_m$ which is chosen to be equal to the length of the receiver section (37A in FIG. 6) of the antenna. The vertical axis in FIG. 7 is the time axis and each scale increment is equal to one measurement time $T_m$. For purposes of the present disclosure, a measurement cycle may be defined as all the NMR RF current pulses and measurements made during $T_m$. FIG. 7 shows different positions of the instrument as it moves through different measurement cycles. Each measurement cycle is labelled with a different frequency ($f_1$ through $f_4$) each of which corresponds to a different radial depth or shell (as originally shown with 38-1 through 38-4 in FIG. 2B) in the formation for a multi-frequency well logging instrument having a magnet (36 in FIG. 2B) which has a magnetic field with an amplitude variation with respect to lateral distance from the magnet, but with substantially constant amplitude over a selected pre-polarization length thereof. Different frequencies may be selected such that the respective measurement regions 62-66 are closely spaced in the radial direction as long as the radial spacing between adjacent excited and measurement regions is sufficiently large so that RF pulses emitted at one frequency do not disturb the static magnetization in regions corresponding to any of the other frequencies. Such result may be obtained by using shaped RF pulses (e.g., and without limitation to limit the effective RF bandwidth) Pulse shaping is a standard NMR technique that includes adjusting the amplitude and phase of the RF pulses at a given frequency to ensure they do not degrade magnetization in regions to be sampled by RF pulses at other frequencies.

In the present example embodiment shown in FIG. 7 the lower third of the RF antenna is used to receive the spin-echo signals whereas the entire antenna is used to transmit 90° and 180° RF pulses. During well logging, measurements are repeated using four, closely spaced measurement regions 62-66 and $vT_m=l_a/3$ where $T_m$ is the measurement time, v represents the instrument speed, and $l_a$ represents the antenna length. The positions of the instrument at the beginning and at the end of each measurement cycle (e.g., for any individual set of RF pulses and signal detection sequence) are indicated at 70, 71A, 71B, 72A, 72B, 73A, 73B, 74A, 74B, and 75, where the end of one measurement and the beginning of the subsequent measurement may be made at the same instrument position (e.g., 71A, 71B, 72A, 72B, 73A, 73B, 74A, and 74B) by starting the subsequent measurement using a different frequency for the RF pulses than the previous measurement. Using the foregoing technique the excitation and measurement regions in the subsequent measurement cycle are substantially unaffected by RF pulse transmission from the prior measurement. In the foregoing discussion, for cases when the antenna sensitive region is different from the physical antenna length, the antenna sensitive region is considered to be the excitation region.

It may be useful to explain in more detail the tool motion and measurements shown in FIG. 7. The measurement starts at the extreme left of FIG. 7 at longitudinal position 70 with a measurement made at a first frequency $f_1$ and thus in a measurement region 62 during receiving RF signals induced by NMR phenomena. During the measurement time $T_m$ the instrument moves from position 70 to the position 71A. The position of 71A is located at a longitudinal distance from the first position 70 equal to $v \cdot T_m$. The measurement region 62 annotated with $f_1$ indicates the formation region from which the received spin-echo signals were acquired during the first measurement. At the end of the first measurement the frequency of the transmitter is rapidly changed to $f_2$ and a new measurement starts on the second measurement region 63, but with the instrument still substantially at the same axial position as 71A, now indicated by 71B. The slight axial movement between 71A and 71B is the result of a frequency switching time which is short and is negligible compared to $T_m$. The measurement region 63 annotated with $f_2$ shows the formation region from which the received spin-echo signals were acquired during the second measurement. Similarly, at the end of the second measurement, with the instrument at a third axial position 72A the transmitter frequency is rapidly switched to a third frequency $f_3$ and a new measurement starts on the third measurement region 64 with the instrument still at the third axial position 72B. It may be observed in FIG. 7, that using an effective receiver antenna length of $vT_m=l_a/3$, at the end of the third measurement the lower part of the antenna overlaps part of the axial region measured during the first measurement. Therefore another measurement may be made on a fourth measurement region (e.g., at 65) before a new measurement made with fully pre-polarized nuclei can be made once again in the first frequency shell (shown as measurement region 66). Thus at the end of the third measurement the frequency of the transmitter is rapidly changed to $f_4$ and a new measurement starts on the fourth frequency shell, e.g., in measurement region 65). At the end of the fourth measurement, the transmitter frequency may be rapidly switched back to $f_1$ and the process repeats until an entire axial region of interest has been measured. As may be inferred from FIG. 7, the fractional length of the receiver portion (37A in FIG. 6) of the antenna, or separate receiver antenna (37B in FIG. 6A), may be a fraction of the length of the antenna, which in turn is related to the speed of motion of the well logging instrument and the number of different RF frequencies desired to excite different regions of the formation, that is:

$$vT_m=l_a/x \qquad (15)$$

where x may be at least 2 (in embodiments where only integer values are used, however it should be noted that non-integral values can be used as well) to eliminate both the $T_1$ and $T_2$ speed effects, and additionally the desired number of RF frequencies may be at least x+1, that is, the minimum choice of frequencies is 3. However, the relationship 15 is not limited only to integer values nor that the measurement region and $vT_m$ are equal. For example, the measurement region may be ⅓ of $l_a$ while the distance traveled in one measurement cycle $vT_m$ is ⅔ of $l_a$. Further, a different number frequencies may be chosen according to a desired pulsing scheme, a desired change in vertical resolution, or a petrophysical consideration for measuring multiple depths into the formation. The scope of the present disclosure is not limited by such considerations.

A few observations and comments using the multi-frequency NMR measurements shown in FIG. 7 are instructive. Successive measurements are adjacent in the axial direction so there are no missed axial zones of the formation. There is no delay between successive measurements apart from the time for switching frequencies (which is negligible compared to typical NMR wait times between measurements) so that the duty cycle of the transmitter will be higher than that used in NMR well logging instruments known in the art. Each of the measurements shown in FIG. 7 may be from within a sensitive volume that is fully pre-polarized by a magnet as described above. The rapid switching of transmitter frequencies may be performed using well known solid state switches. The example shown in FIG. 7 is for the case where the length of the receiver section of the antenna is one third of the total antenna length, e.g., $v \cdot T_m=l_a/3$ which uses four frequencies to obtain a properly polarized suite of axially continuous measurements. In general, if $v \cdot T_m=l_a/n$ where n=2, 3, . . . then n+1 frequencies or more may be used to obtain an properly polarized suite of axially continuous measurements. The order of frequencies does not necessarily have to be monotonically increasing or decreasing. In embodiments, the measurement region does not move substantially beyond the initial excitation region for a particular transmitter antenna length 37. It is possible that some combination of the distance $vT_m$, the excitation region, and the measurement region will result in some or all of the receiver section moving beyond the initial excitation region, and thus $T_2$ speed effects will occur. Unintended variable speeds are one cause of such cases. The present disclosure applies to any measurement method known to those skilled in the art which involves a preparation pulse or set of pulses (for example the 90 degree and 180 degrees pulses) applied to the transmitter length, and measurement events (for example the receiving of the echo signals) in the measurement region. Examples include saturation recovery sequences, inversion recovery sequences, composite pulse sequences, relaxometry sequences, and alike. A specific case is discussed next.

Consider a specific example of the antenna and RF pulse sequence shown in FIG. 7 for a well logging instrument moving at a speed of 6 inches per second (1800 feet per hour). If the receiver section (37A in FIG. 6A) of the RF antenna has a length of 6 inches then the antenna length may be 18 inches and the measurement time $T_m=1$ second. During the measurement time a pulse sequence, e.g., a Carr-Purcell-Meiboom-Gill (CPMG) pulse sequence with 5000 spin echoes (caused by 5000 180° RF pulses following an initial 90° RF excitation pulse) may be acquired using an echo spacing TE of $0.2\times10^{-1}$ s. In some embodiments, a set of CPMG sequences can be operated after the first main CPMG sequence having fewer spin echoes and a plurality of, e.g., 10 short wait time (e.g., 0.02 s) measurement sequences each having a relatively small number of spin echoes (e.g., 20). These sets of CPMG sequences are sometimes referred to as bursts or trainlets, and the present disclosure includes potentially choosing the measurement cycle to include these bursts and any other plurality of pulses. If a longer measurement time is desired in some embodiments the receiver section of the antenna may be a larger fraction of the total length of the antenna, e.g., one-half of the total antenna length, $v \cdot T_m = l_a/2$ which increases the measurement time to 1.5 seconds for an 18 inch antenna and an instrument speed of 6 inches per second. Using such longer receiver antenna (or receiver section of the transmit/receive antenna as explained above) would use three different RF frequencies as discussed above. Other embodiments may comprise a longer or shorter total antenna length. Other embodiments of antenna design and measurement sequences may be used that are within the scope of the present disclosure.

NMR spin-echo well logging measurements are typically acquired as phase alternated pairs (i.e., the phases of the 90° pulses in two phase alternated pair CPMG sequences are shifted by a phase angle of 180° and they are then subtracted from each other) in order to cancel baseline offsets in the CPMG spin echo signals. For the measurements shown schematically in FIG. 7 subsequent measurements at the same frequency may be one antenna length apart and could be acquired as phase alternated pairs, or measurements at the different closely spaced frequencies could be acquired with alternating phases and combined. In some embodiments, the offsets could be accounted for in the data processing (See, Freedman, U.S. Pat. No. 6,838,875). The method for removing the offsets is not intended to limit the scope of the present disclosure.

The present disclosure is practiced with a magnetic field profile that allows measurement frequencies to excite different regions of the formation. The frequencies can be chosen to excite formation regions which are closely spaced, so that formation properties do not change substantially. In this case the formation is fully covered by measurements and those measurements are free from the Tz speed effect. In some other embodiments, at a cost of coverage of the formation, the frequencies can be chosen intentionally further apart so as to benefit from measuring the formation properties as a function of distance from the tool face. Again, the measurements are free of the Tz speed effect. The disclosure also applies to single frequency operation of any magnetic field and antenna design at a cost of coverage of the formation. In all cases, the present disclosure represents an improvement in removing the Tz speed effect.

In various embodiments according to the present disclosure, associated RF pulse sequences for fast NMR logging using an instrument as explained above may have one or more of the following properties: (1) substantially no $T_2$ speed effect, (2) substantially no longitudinal part of the formations is unmeasured, (3) standard $T_2$, $T_1$ and/or diffusion based inversion methods are applicable, and (4) all measured nuclear spins are pre-polarized by a long pre-polarization magnet.

Although the preceding description has been described herein with reference to particular means, materials and embodiments, it is not intended to be limited to the particulars disclosed herein; rather, it extends to all functionally equivalent structures, methods and uses, such as are within the scope of the appended claims.

What is claimed is:

1. An apparatus for measuring nuclear magnetic resonance (NMR) properties of subsurface formations, comprising:
   a magnet having a selected length for pre-polarizing nuclear spins in the formations;
   a transmitter antenna;
   at least one of a receiver section of the transmitter antenna and a separate receiver antenna having a length along the longitudinal dimension of the apparatus which is shorter than a length of the transmitter antenna along the longitudinal dimension; and
   circuitry for applying radio frequency current pulses to the entire transmitter antenna and for receiving signals by the at least one of the receiver section of the transmitter antenna and the separate receiver antenna;
   wherein the circuitry comprises a multiple frequency transmitter, and wherein the circuitry is configured to successively apply radio frequency current pulses through the entire transmitter antenna at each of a plurality of different frequencies; and
   wherein the circuitry is configured to shape the current pulses such that magnetization of the formations is substantially undisturbed other than in a region having a static magnetic field amplitude corresponding to the frequency of the current pulses being transmitted.

2. The apparatus of claim 1 wherein the successively applied radio frequency current pulses at each of the plurality of frequencies is performed with substantially no delay between the end of the current pulses at one frequency and the beginning of the current pulses at the successive frequency.

3. The apparatus of claim 1 wherein the transmitter antenna length is an integer multiple of the at least one of the receiver section of the transmitter antenna and the separate receiver antenna.

4. The apparatus of claim 3 wherein the integer multiple is one less than a number of different frequencies generated by the circuitry for applying radio frequency pulses to the transmitter antenna.

5. The apparatus of claim 4 wherein the product of a number of measurement cycles, a speed of motion of the apparatus, and a measurement cycle time Tm are chosen such that their product is substantially equal to the transmitter antenna length.

6. The apparatus of claim 1 wherein the circuitry is configured to passively or actively disable a remainder of the transmitter antenna.

7. The apparatus of claim 1 wherein the magnet is configured to induce a static magnetic field having a substantially constant amplitude at a selected lateral distance from the magnet along a longitudinal direction at least equal in length to a length of the transmitter antenna.

8. The apparatus of claim 7 wherein the magnet is configured such that the substantially constant amplitude is related to a lateral distance from the magnet within a selected lateral distance range.

9. The apparatus of claim 1 wherein the apparatus is configured to be moved along a wellbore using at least one of armored electrical cable, a drilling assembly, tractor, coiled tubing and slickline.

10. The apparatus of claim 1 wherein the transmitter antenna and the separate receiver antenna comprise coaxially aligned coils.

11. A method for measuring nuclear magnetic resonance (NMR) properties of subsurface formations, comprising:
   inducing a static magnetic field in the formation for pre-polarizing nuclear spins;
   passing a plurality of radio frequency current pulses through a transmitter antenna; and
   detecting NMR signals, the detecting performed by at least one of a receiver portion of the transmitter antenna and a separate receiver antenna, the at least one of a receiver section and the separate receiver antenna having a length which is shorter than a length of the transmitter antenna along a longitudinal dimension of the transmitter antenna;
   wherein each of the plurality current pulses is shaped such that magnetization of the formations is substantially undisturbed other than in a region having a static magnetic field amplitude corresponding to the frequency of the plurality of current pulses.

12. The method of claim 11 wherein the plurality of radio frequency current pulses are applied successively at each of a plurality of different frequencies corresponding to a plurality of measurement cycles.

13. The method of claim 11 wherein the plurality of radio frequency current pulses comprises at least one pulse sequence having a first number of current pulses and at least one pulse sequence having a second number of current pulses smaller than the first number.

14. The method of claim 11 wherein the static magnetic field has substantially constant amplitude in a longitudinal direction at a selected lateral distance into the subsurface formations.

15. The method of claim 14 wherein the amplitude of the static magnetic field is related to the lateral distance from the magnet.

16. The method of claim 11 wherein a sensitivity distribution of the transmitter antenna is different from a longitudinal length of the transmitter antenna.

17. The method of claim 16 wherein the plurality of radio frequency current pulses are applied successively at each of a plurality different frequencies during each of a plurality of measurement cycles.

18. An apparatus for measuring nuclear magnetic resonance (NMR) properties of subsurface formations, comprising:
   a magnet having a selected length for pre-polarizing nuclear spins in the formations;
   a transmitter antenna;
   at least one of a receiver section of the transmitter antenna and a separate receiver antenna having a length along the longitudinal dimension of the apparatus which is shorter than a length of the transmitter antenna along the longitudinal dimension; and
   circuitry for applying radio frequency current pulses to the entire transmitter antenna and for receiving signals by the at least one of the receiver section of the transmitter antenna and the separate receiver antenna;
   wherein the transmitter antenna length is an integer multiple of the at least one of the receiver section of the transmitter antenna and the separate receiver antenna, and wherein the integer multiple is one less than a number of different frequencies generated by the circuitry for applying radio frequency pulses to the transmitter antenna.

19. The apparatus of claim 18 wherein the product of a number of measurement cycles, a speed of motion of the apparatus, and a measurement cycle time Tm are chosen such that their product is substantially equal to the transmitter antenna length.

* * * * *